(12) United States Patent
Choi et al.

(10) Patent No.: US 9,155,512 B2
(45) Date of Patent: Oct. 13, 2015

(54) SYSTEMS AND METHODS FOR PREDICTING CORONARY PLAQUE VULNERABILITY FROM PATIENT-SPECIFIC ANATOMIC IMAGE DATA

(71) Applicant: HeartFlow, Inc., Redwood City, CA (US)

(72) Inventors: Gilwoo Choi, Menlo Park, CA (US); Leo Grady, Millbrae, CA (US); Michiel Schaap, Mountain View, CA (US); Charles A. Taylor, San Mateo, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

(21) Appl. No.: 14/254,521

(22) Filed: Apr. 16, 2014

(65) Prior Publication Data

US 2015/0164453 A1 Jun. 18, 2015

Related U.S. Application Data

(60) Provisional application No. 61/917,639, filed on Dec. 18, 2013.

(51) Int. Cl.
*A61B 5/00* (2006.01)
*A61B 6/00* (2006.01)

(52) U.S. Cl.
CPC ............. *A61B 6/503* (2013.01); *A61B 6/5217* (2013.01)

(58) Field of Classification Search
CPC ..... G06F 19/70; G06F 19/3437; A61B 6/504; A61B 5/02007; A61B 5/026; A61B 6/503; A61B 8/06; G01R 33/56366; G06T 2207/30104; G06T 2211/404
USPC .......................... 600/407–480; 382/128–132
See application file for complete search history.

(56) References Cited

U.S. PATENT DOCUMENTS

| | | | |
|---|---|---|---|
| 2006/0149522 A1 | 7/2006 | Tang | |
| 2010/0278405 A1 | 11/2010 | Kakadiaris et al. | |
| 2010/0298719 A1* | 11/2010 | Kock et al. | 600/485 |
| 2012/0041318 A1* | 2/2012 | Taylor | 600/504 |
| 2012/0041320 A1* | 2/2012 | Taylor | 600/508 |
| 2012/0041323 A1* | 2/2012 | Taylor et al. | 600/508 |
| 2012/0041735 A1* | 2/2012 | Taylor | 703/9 |
| 2012/0041739 A1* | 2/2012 | Taylor | 703/11 |
| 2012/0053918 A1* | 3/2012 | Taylor | 703/9 |
| 2012/0053919 A1* | 3/2012 | Taylor | 703/9 |
| 2012/0243761 A1* | 9/2012 | Senzig et al. | 382/131 |
| 2014/0236492 A1* | 8/2014 | Taylor | 702/19 |

* cited by examiner

*Primary Examiner* — Sanjay Cattungal
(74) *Attorney, Agent, or Firm* — Bookoff McAndrews, PLLC

(57) ABSTRACT

Systems and methods are disclosed for predicting coronary plaque vulnerability, using a computer system. One method includes acquiring anatomical image data of at least part of the patient's vascular system; performing, using a processor, one or more image characteristics analysis, geometrical analysis, computational fluid dynamics analysis, and structural mechanics analysis on the anatomical image data; predicting, using the processor, a coronary plaque vulnerability present in the patient's vascular system, wherein predicting the coronary plaque vulnerability includes calculating an adverse plaque characteristic based on results of the one or more of image characteristics analysis, geometrical analysis, computational fluid dynamics analysis, and structural mechanics analysis of the anatomical image data; and reporting, using the processor, the calculated adverse plaque characteristic.

20 Claims, 7 Drawing Sheets

SYSTEMS AND METHODS FOR PREDICTING CORONARY PLAQUE VULNERABILITY FROM PATIENT-SPECIFIC ANATOMIC IMAGE DATA

RELATED APPLICATION(S)

This application claims priority to U.S. Provisional Application No. 61/917,639 filed Dec. 18, 2013, the entire disclosure of which is hereby incorporated by reference in its entirety.

FIELD OF THE INVENTION

Various embodiments of the present disclosure relate generally to medical imaging and related methods. More specifically, particular embodiments of the present disclosure relate to systems and methods for predicting coronary plaque vulnerability from patient-specific anatomic image data.

BACKGROUND

Coronary artery disease may produce coronary lesions in the blood vessels providing blood to the heart, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack.

Patients suffering from chest pain and/or exhibiting symptoms of coronary artery disease may be subjected to one or more tests that may provide some indirect evidence relating to coronary lesions. For example, noninvasive tests may include electrocardiograms, biomarker evaluation from blood tests, treadmill tests, echocardiography, single positron emission computed tomography (SPECT), and positron emission tomography (PET). Anatomic data may be obtained noninvasively using coronary computed tomographic angiography (CCTA). CCTA may be used for imaging of patients with chest pain and involves using computed tomography (CT) technology to image the heart and the coronary arteries following an intravenous infusion of a contrast agent.

Meanwhile, vulnerable plaque features, such as adverse plaque characteristics (APCs)), have been actively investigated for prognosis of major adverse cardiac events (MACE) using both invasive and noninvasive techniques, such as intravascular ultrasound (IVUS), optical coherence tomography (OCT), and coronary computed tomography data (CCTA).

However, a need exists for systems and methods for predicting coronary plaque vulnerability from patient-specific anatomic image data.

SUMMARY

According to certain aspects of the present disclosure, systems and methods are disclosed for predicting coronary plaque vulnerability from patient-specific anatomic image data. One method includes: acquiring anatomical image data of at least part of the patient's vascular system; performing, using a processor, one or more image characteristics analysis, geometrical analysis, computational fluid dynamics analysis, and structural mechanics analysis on the anatomical image data; predicting, using the processor, a coronary plaque vulnerability present in the patient's vascular system, wherein predicting the coronary plaque vulnerability includes calculating an adverse plaque characteristic based on results of the one or more image characteristics analysis, geometrical analysis, computational fluid dynamics analysis, and structural mechanics analysis of the anatomical image data; and reporting, using the processor, the calculated adverse plaque characteristic.

In accordance with another embodiment, a system for reporting coronary plaque vulnerability from patient-specific anatomic image data, comprises: a data storage device storing instructions for predicting coronary plaque vulnerability from patient-specific anatomic image data; and a processor configured for: acquiring anatomical image data of at least part of the patient's vascular system; performing, using a processor, one or more image characteristics analysis, geometrical analysis, computational fluid dynamics analysis, and structural mechanics analysis on the anatomical image data; predicting, using the processor, a coronary plaque vulnerability present in the patient's vascular system, wherein predicting the coronary plaque vulnerability includes calculating an adverse plaque characteristic based on results of the one or more image characteristics analysis, geometrical analysis, computational fluid dynamics analysis, and structural mechanics analysis of the anatomical image data; and reporting, using the processor, the calculated adverse plaque characteristic.

In accordance with yet another embodiment, a non-transitory computer readable medium for use on a computer system containing computer-executable programming instructions for performing a method of reporting coronary plaque vulnerability from patient-specific anatomic image data is provided. The method includes: acquiring anatomical image data of at least part of the patient's vascular system; performing, using a processor, one or more image characteristics analysis, geometrical analysis, computational fluid dynamics analysis, and structural mechanics analysis on the anatomical image data; predicting, using the processor, a coronary plaque vulnerability present in the patient's vascular system, wherein predicting the coronary plaque vulnerability includes calculating an adverse plaque characteristic based on results of the one or more image characteristics analysis, geometrical analysis, computational fluid dynamics analysis, and structural mechanics analysis of the anatomical image data; and reporting, using the processor, the calculated adverse plaque characteristic.

Another method includes: acquiring anatomical image data of at least part of the patient's vascular system; performing, using a processor, one or more image characteristics analysis, geometrical analysis, computational fluid dynamics analysis, and structural mechanics analysis on the anatomical image data; and predicting, using the processor, a probability of an adverse cardiac event from coronary plaque vulnerability present in the patient's vascular system based on results of the one or more image characteristics analysis, geometrical analysis, computational fluid dynamics analysis, and structural mechanics analysis of the anatomical image data.

In accordance with another embodiment, a system of predicting coronary plaque vulnerability from patient-specific anatomic image data, comprises: a data storage device storing instructions for predicting coronary plaque vulnerability from patient-specific anatomic image data; and a processor configured to: to execute the instructions to perform a method including: acquiring anatomical image data of at least part of the patient's vascular system; performing, using a processor, one or more image characteristics analysis, geometrical analysis, computational fluid dynamics analysis, and structural mechanics analysis on the anatomical image data; and predicting, using the processor, a probability of an adverse cardiac event coronary plaque vulnerability present in the patient's vascular system, based on results of the one or more image characteristics analysis, geometrical analysis, computational fluid dynamics analysis, and structural mechanics analysis of the anatomical image data.

In accordance with yet another embodiment, a non-transitory computer readable medium for use on a computer system containing computer-executable programming instructions for predicting coronary plaque vulnerability from patient-specific anatomic image data is provided. The method includes: acquiring anatomical image data of at least part of the patient's vascular system; performing, using a processor, one or more image characteristics analysis, geometrical analysis, computational fluid dynamics analysis, and structural mechanics analysis on the anatomical image data; and predicting, using the processor, a probability of an adverse cardiac event coronary plaque vulnerability present in the patient's vascular system, based on results of the one or more image characteristics analysis, geometrical analysis, computational fluid dynamics analysis, and structural mechanics analysis of the anatomical image data.

Yet another method includes: acquiring anatomical image data of at least part of a patient's vascular system; performing, using a processor, one or more of image characteristics analysis, geometrical analysis, computational fluid dynamics analysis, and structural mechanics analysis on the anatomical image data; predicting, using the processor, a coronary plaque vulnerability present in the patient's vascular system based on results of one or more of the image characteristics analysis, geometrical analysis, computational fluid dynamics analysis, and structural mechanics analysis of the anatomical image data; modifying one or more of the image characteristics analysis, geometrical analysis, computational fluid dynamics analysis, and structural mechanics analysis on the anatomical image data based on a proposed treatment; and determining an effect of the treatment on the prediction of the coronary plaque vulnerability based on the modified one or more of the image characteristics analysis, geometrical analysis, computational fluid dynamics analysis, and structural mechanics analysis on the anatomical image.

In accordance with another embodiment, a system of determining the effect of a treatment on coronary plaque vulnerability, comprises: a data storage device storing instructions for predicting coronary plaque vulnerability from patient-specific anatomic image data; and a processor configured to execute the instructions to perform a method including: acquiring anatomical image data of at least part of the patient's vascular system; performing, using a processor, one or more of image characteristics analysis, geometrical analysis, computational fluid dynamics analysis, and structural mechanics analysis on the anatomical image data; predicting, using the processor, a coronary plaque vulnerability present in the patient's vascular system based on results of one or more of the image characteristics analysis, geometrical analysis, computational fluid dynamics analysis, and structural mechanics analysis of the anatomical image data; modifying one or more of the image characteristics analysis, geometrical analysis, computational fluid dynamics analysis, and structural mechanics analysis on the anatomical image data based on a proposed treatment; and determining an effect of the treatment on the prediction of the coronary plaque vulnerability based on the modified one or more of the image characteristics analysis, geometrical analysis, computational fluid dynamics analysis, and structural mechanics analysis on the anatomical image.

In accordance with yet another embodiment, a non-transitory computer readable medium for use on a computer system containing computer-executable programming instructions for performing a method of determining the effect of a treatment on coronary plaque vulnerability is provided. The method comprises: acquiring anatomical image data of at least part of the patient's vascular system; performing, using a processor, one or more of image characteristics analysis, geometrical analysis, computational fluid dynamics analysis, and structural mechanics analysis on the anatomical image data; predicting, using the processor, a coronary plaque vulnerability present in the patient's vascular system based on results of one or more of the image characteristics analysis, geometrical analysis, computational fluid dynamics analysis, and structural mechanics analysis of the anatomical image data; modifying one or more of the image characteristics analysis, geometrical analysis, computational fluid dynamics analysis, and structural mechanics analysis on the anatomical image data based on a proposed treatment; and determining an effect of the treatment on the prediction of the coronary plaque vulnerability based on the modified one or more of the image characteristics analysis, geometrical analysis, computational fluid dynamics analysis, and structural mechanics analysis on the anatomical image.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

As described above, a new generation of noninvasive tests have been developed to assess blood flow characteristics. These noninvasive tests use patient imaging (such as CT) to determine a patient-specific geometric model of blood vessels, which may be used computationally to simulate blood flow using computational fluid dynamics (CFD) along with appropriate physiological boundary conditions and parameters. Examples of inputs to these patient-specific boundary conditions include the patient's blood pressure, blood viscosity, and the expected demand of blood from supplied tissue (derived from scaling laws and a mass estimation of the supplied tissue from the patient imaging).

The present disclosure is directed to a new approach for providing prognosis of adverse cardiac events and for guiding medical therapy based on patient-specific geometry and blood flow characteristics. Although the present disclosure is described with respect to coronary artery disease, the same system is applicable to creating a patient-specific prediction of rupture risks in other vascular systems beyond the coronary arteries, such as the carotid artery.

More specifically, the present disclosure is directed to using patients' cardiac imaging to derive a patient-specific geometric model of the coronary vessels. Coronary flow simulations with respect to patient physiological information and estimated boundary conditions may then be performed on the model to extract hemodynamic characteristics. The hemodynamic characteristics may be used to predict cardiac events, including plaque rupture and/or myocardial infarction. The present disclosure may use physics-based simulation of blood flow to predict those cardiac events. In addition, the present disclosure includes the use of machine learning or rule-based methods to achieve the predictions. Furthermore, the machine-learning and rule-based methods may incorporate various risk factors, including patient demographics, biomarkers, and/or coronary geometry, as well as the results of patient-specific biophysical simulations (e.g., hemodynamic characteristics). If additional diagnostic test results are available, those results can be used to train a machine-learning algorithm, for example, in making a prediction. Several predictions may be made based on the processing described. Specifically, the present disclosure provides a system and method for prediction and/or report of: (i) adverse plaque characteristics; (ii) cardiac risk (or cardiac risk-related features); and (iii) change of risk factors in response to various medical treatment protocols to guide medical therapy planning.

Figure 1:
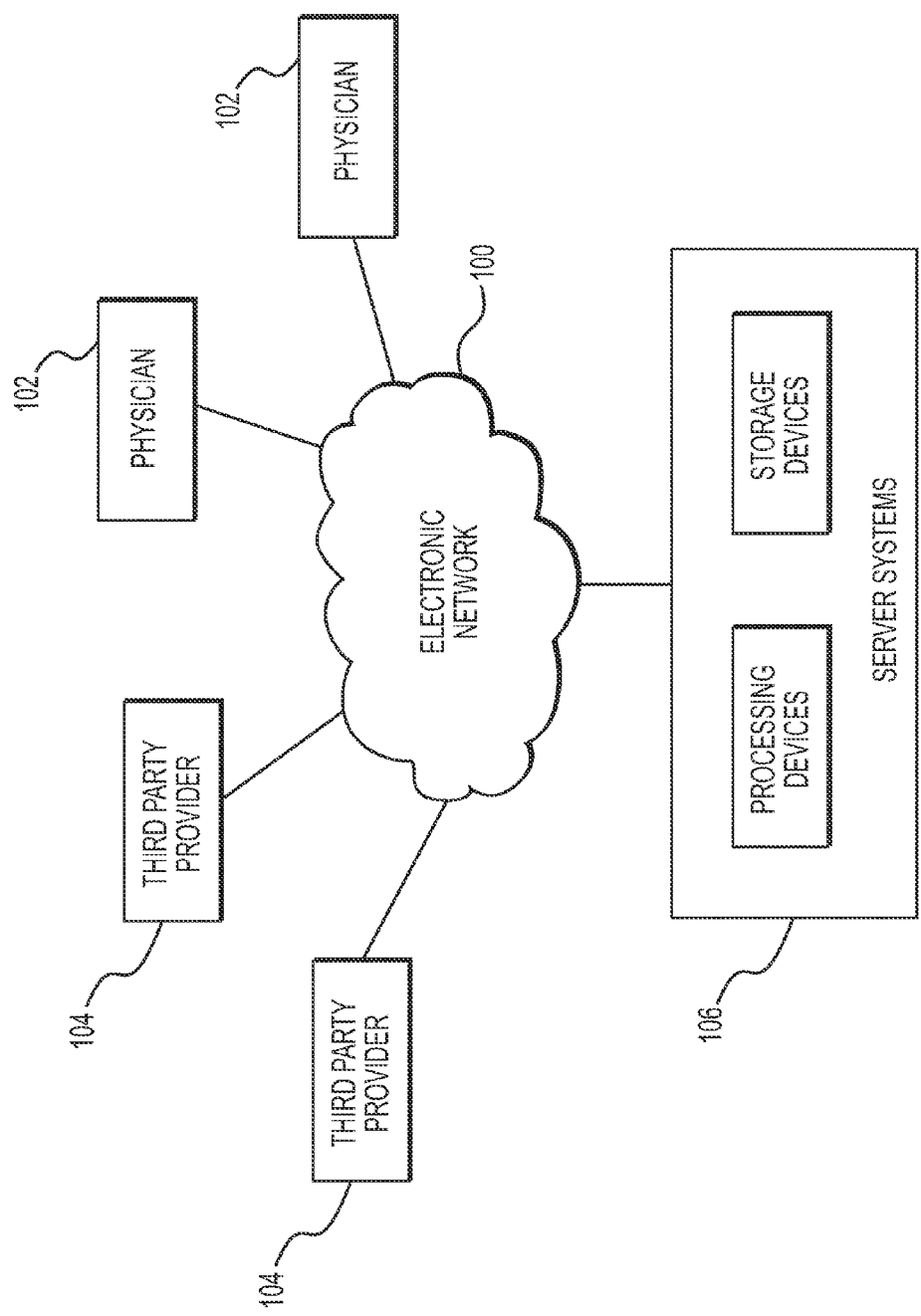
FIG. 1 is a block diagram of an exemplary system and network for predicting coronary plaque vulnerability from patient-specific anatomic image data, according to an exemplary embodiment of the present disclosure.

Referring now to the figures, FIG. 1 depicts a block diagram of an exemplary system and network for predicting coronary plaque vulnerability from patient-specific anatomic image data. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' cardiac and/or vascular systems. The physicians 102 and/or third party providers 104 may also obtain any combination of patient-specific information, such as age, medical history, blood pressure, blood viscosity, etc. Physicians 102 and/or third party providers 104 may transmit the cardiac/vascular images and/or patient-specific information to server systems 106 over the electronic network 100. Server systems 106 may include storage devices for storing images and data received from physicians 102 and/or third party providers 104. Server systems 106 may also include processing devices for processing images and data stored in the storage devices.

Figure 2:
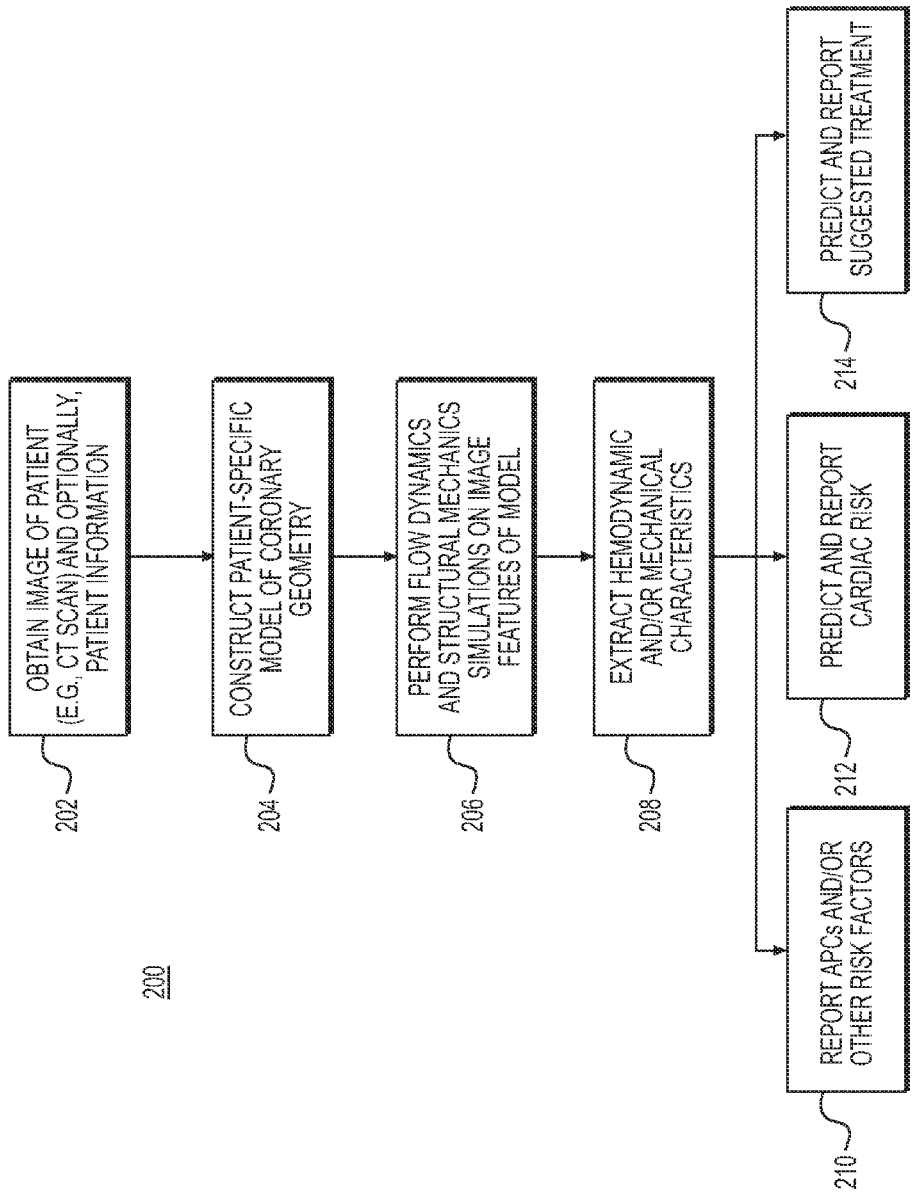
FIG. 2 is a block diagram of an exemplary method for predicting coronary plaque vulnerability from patient-specific anatomic image data, according to an exemplary embodiment of the present disclosure.

FIG. 2 is a block diagram of an exemplary method 200 for predicting coronary plaque vulnerability from patient-specific anatomic image data, according to an exemplary embodiment of the present disclosure. Method 200 may be performed by server systems 106, based on information, images, and data received from physicians 102 and/or third party providers 104 over electronic network 100. The method of FIG. 2 may include acquiring a model of coronary geometry and performing analysis using the model in order to predict plaque vulnerability and draw conclusions based on those predictions. As shown in FIG. 2, in general, method 200 may include obtaining patient-specific information (e.g., CT scan images, phenotype information, etc.) (step 202), constructing a patient-specific geometric model (step 204), performing flow dynamics and structural mechanics simulations on geometrical features and image features of the model, and extracting hemodynamic and mechanical characteristics (step 206). Based on the extracted characteristics and features, the server systems 106 may then perform step 208 to predict and/or report adverse plaque characteristics (APCs) (step 210). Further detail of one embodiment of step 210 is provided in FIG. 3, in which metrics for computing APCs are determined, and metric values are found for specific patients, in order to determine APCs associated with the patients.

In another embodiment, performing step 208 may cause server systems 106 to further predict and/or report cardiac risk or cardiac risk-related features (e.g., predicting plaque rupture or occurrence of myocardial infarction) (step 212). For example, FIGS. 4A and 4B describe one embodiment of step 212 in more detail, in which feature vectors are created for points in the patient-specific geometric model and probability of plaque rupture or MI event is estimated by analyzing feature weights. In yet another embodiment, server systems 106 may predict and/or report optimal treatment protocols in response to the risk (step 214). For example, FIGS. 5A and 5B provide more detail on one embodiment of step 214 by describing how to find the impact of various medical therapy protocols and/or lifestyle modifications on risk factor prediction.

Thus, in one embodiment, method 200 may employ a patient-specific model of coronary geometry to predict and report one or more of APCs, cardiac risk, and/or treatment. Method 200 may include obtaining a patient-specific geometric model (step 202) comprising a digital representation (e.g., the memory or digital storage (including a hard drive and/or network drive) of a computational device such as a computer, laptop, DSP, server, etc.). The coronary geometry may be represented as a list of points in space, possibly with a list of neighbors for each point, in which the space can be mapped to spatial units between points (e.g., millimeters).

In one embodiment, step 202 may comprise obtaining the model, such as by constructing a patient-specific model of coronary geometry, for instance, by modeling a patient's coronary vasculature, including one or more lumens, plaque, and/or lumen walls (step 204). Given a 3-D image of coronary vasculature, many methods exist for extracting a model of cardiovascular geometry pertaining to a specific patient. The patient-specific model may be constructed or rendered based on images, such as CT scans associated with a patient. In one embodiment, the model may be derived by performing a cardiac CT in the end of a diastole phase of the cardiac cycle, for instance, using Black-Blood Magnetic Resonance Imaging. The image may be segmented manually or automatically to identity voxels belonging to areas of interest. Inaccuracies in the geometry may be extracted automatically and optionally corrected by a human observer. For instance, a human observer may compare the extracted geometry with the CT images and make corrections as needed. Once voxels are identified, the geometric model can be derived (e.g., using marching cubes). Step 204 may include all the components necessary to construct a patient-specific model.

Once a model is available, step 206 may include performing various physics-based simulations on the model to derive conclusions relating to coronary plaque vulnerability. Such conclusions may include, for example, predicting and reporting on cardiac risk and proposed treatment. In one embodiment, method 200 may employ machine learning or rule-based methods that incorporate various risk factors, including patient demographics, biomarkers, coronary geometry, as well as the results of patient-specific biophysical simulations (e.g., hemodynamic characteristics). Additional diagnostic test results may also be used to train the machine learning algorithms for better predictions. Step 208 may then use results from step 206 to predict and/or report on (1) adverse plaque characteristics (APCs) (step 210), (2) cardiac risk or cardiac risk-related features (e.g., predicting plaque rupture or occurrence of myocardial infarction) (step 212), and/or (3) optimal treatment protocols in response to the risk (step 214).

Figure 3:
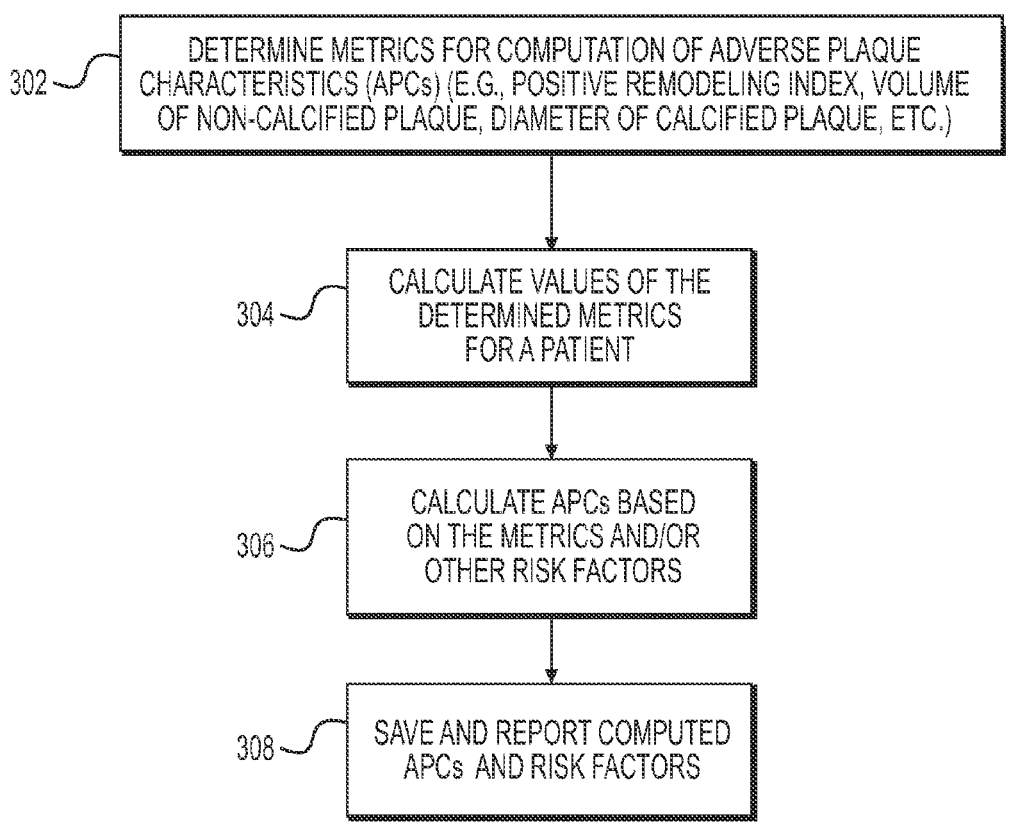
FIG. 3 is a block diagram of an exemplary method for reporting adverse plaque characteristics from patient-specific anatomic image data, according to an exemplary embodiment of the present disclosure.

FIG. 3 is a block diagram of an exemplary method 300 for reporting adverse plaque characteristics (APCs) from a patient-specific model. The method of FIG. 3 may be performed by server systems 106, based on information, images, and/or data received from physicians 102 and/or third party providers 104 over electronic network 100. In one embodiment, method 300 may be performed using a patient-specific model of a patient's coronary vasculature. For example, the patient-specific model may include the geometry for, at least, the patient's coronary artery tree, including the lumen, plaque, and/or lumen walls (i.e., external elastic membrane (EEM) of the coronary arteries). The model may be segmented manually or automatically to identify voxels belonging to the lumen and lumen wall. Wall segmentation may include calcified and non-calcified plaques. In analyzing the model to report adverse plaque characteristics, method 300 may include determining or defining metrics for computing APCs (step 302). Exemplary metrics include: the presence of positive remodeling, low attenuation plaque, spotty intra-plaque calcification, etc. Step 302 may further include determining additional metrics for computation of APCs or prioritizing which metrics to use for computing APCs. Prioritizing metrics in step 302 may be used, for instance, where computational capacity is limited or where time constraints may not permit computing all the metrics. Step 302 may optionally involve computing other risk factors.

Based on the metrics determined in step 302, method 300 may next include calculating values for the metrics (step 304). For instance, step 304 may include executing computations to find control or threshold values, as well as patient-specific values for the metrics. For the constructed lumen and wall geometries of the patient, method 300 may then include automatically calculating values for each metric for use in computing APCs for the constructed lumen and wall geometries of the patient.

For the exemplary metrics, the presence of positive remodeling, the presence of low attenuation plaque, and/or the presence of spotty calcification, step 304 may proceed according to the following description. For example for the presence of positive remodeling metric, step 304 may include, first, detecting stenosis or presence of plaque in a wall segmentation. A segment may be identified as diseased based on the degree of stenosis or amount of plaque. Next, step 304 may include computing a positive remodeling index, for example, by evaluating a cross-sectional area (CSA) of EEM at a lesion and reference CSA based on the following equation:

$$\text{Positive remodeling index} = \frac{CSA \text{ of } EEM \text{ at lesion}}{CSA \text{ of } EEM \text{ at reference}}$$

In one embodiment, the threshold value for a positive remodeling index to indicate the presence of positive remodeling is 1.05. In other words, if the computed, patient positive remodeling index>1.05, step 304 may include reporting that positive remodeling is present. Step 304 may then include reporting that there is, in fact, presence of positive remodeling detected and/or the positive remodeling index. This metric of the positive remodeling index may factor into calculation of APCs. The calculation of APCs may also include determining the presence of low attenuation plaque, for instance, by detecting non-calcified plaques in wall segmentation at a diseased segment. For example, if there exists a region of non-calcified plaque whose intensity is ≤30 Hounsfield Unit (HU), step 304 may include reporting the presence of low attenuation plaque as true and/or the volume of the non-calcified plaque whose intensity is ≤30 HUs.

The calculation of APCs may further include determining the presence of spotty intra-plaque calcification (e.g., using image characteristics analysis to find spotty calcification), such as by detecting calcified plaques in wall segmentation at a diseased segment. Hessian-based eigenvalue analysis may be utilized to detect blob-shaped calcified plaques. If the diameter of intra-lesion nodular calcified plaque 3 mm, then method 300 may include reporting the presence of spotty calcification as true and/or reporting the diameter.

Based on the calculated metrics, step 306 may calculate APCs. Each metric may alone constitute an APC, or the metrics may be combined in a form indicative of collective APCs. Step 306 may optionally involve calculating other risk factors.

Finally, method 300 may include step 308 of saving the results of computed APCs scores and/or other risk factors with images as a digital representation (e.g., the memory or digital storage (e.g., hard drive, network drive) of a computational device such as a computer, laptop, DSP, server, etc.) and making them available to a physician, for instance. In one embodiment, step 308 may include actively reporting APCs and/or other risk factors to physicians. In another embodiment, step 308 may simply prompt or signal to a user that computed APC scores and risk factors are available for viewing and/or verification.

Figure 4A:
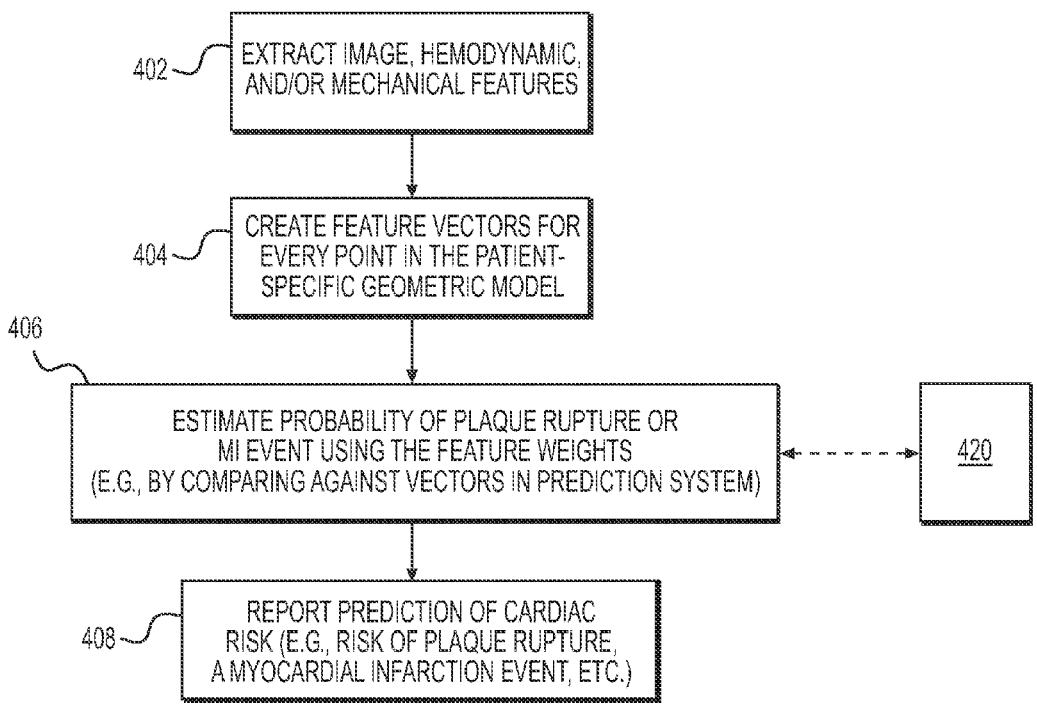
FIG. 4A is a block diagram of an exemplary method for predicting cardiac risk or risk-related features from patient-specific anatomic image data, according to an exemplary embodiment of the present disclosure.
Figure 5A:
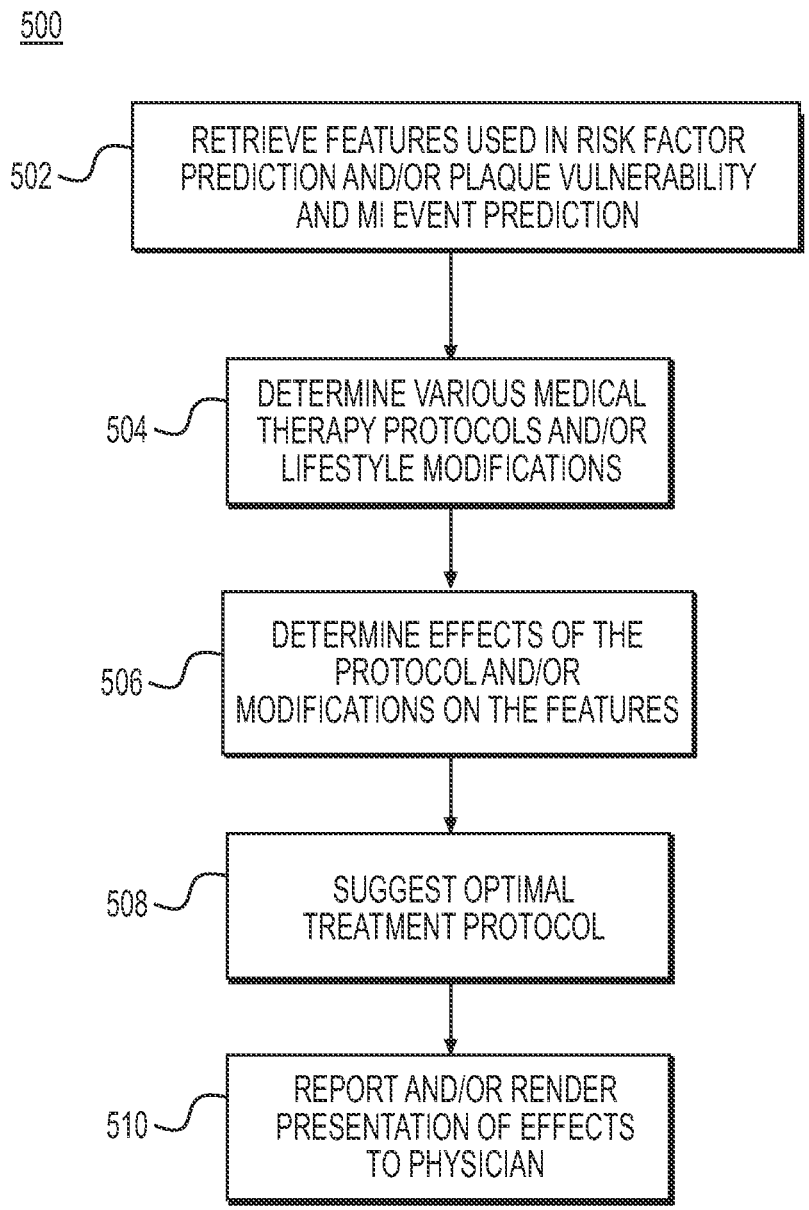
FIG. 5A is a block diagram of an exemplary method for predicting change of cardiac risk or risk-related features in response to medical treatment protocols from patient-specific anatomic image data, according to an exemplary embodiment of the present disclosure.
Figure 5B:
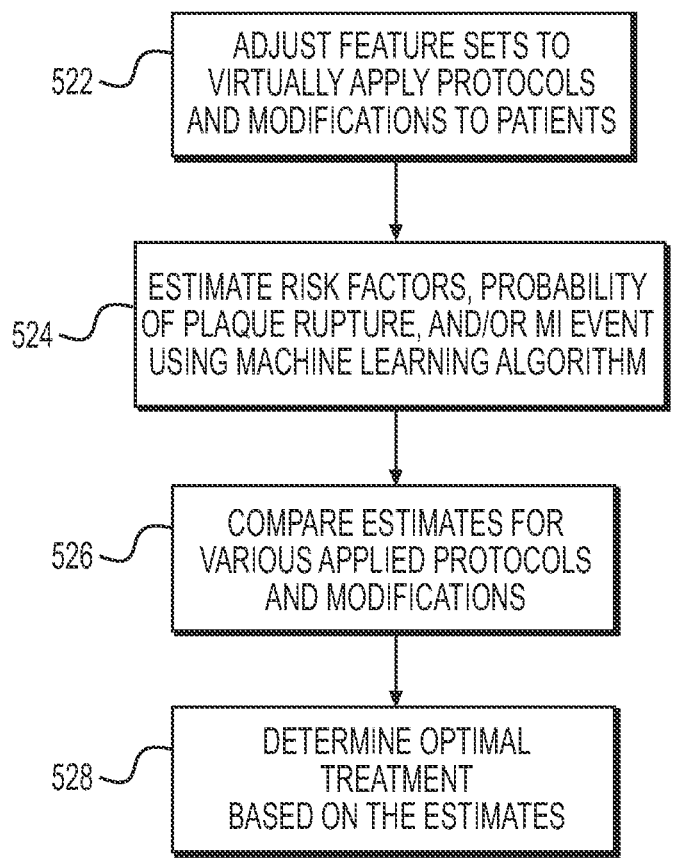
FIG. 5B is a block diagram of an exemplary method for creating and training a prediction system to predict, using patient-specific anatomic image data, change of cardiac risk or risk-related features in response to medical treatment protocols and/or lifestyle modifications, according to an exemplary embodiment of the present disclosure.

FIG. 4A is a block diagram of an exemplary method 400 for predicting cardiac risk or risk-related features based on patient-specific models. The method of FIG. 4A may be performed by server systems 106, based on information, images, and data received from physicians 102 and/or third party providers 104 over electronic network 100. Method 400 may be performed on a patient-specific model including one or more modeled lumens, plaque, lumen walls, left and right myocardium, etc. For instance, the model may describe a patient's ascending aorta, coronary artery tree, myocardium, valves, and chambers. Then, segmenting may help identify voxels belonging to the aorta and the lumen of the coronary arteries.

In one embodiment, method 400 may include constructing the model from the patient image(s) prior to assessing the model for cardiac risk. Furthermore, method 400 may include collecting information, including patient demographics (e.g., age, gender, weight, blood pressure, etc.) and/or biomarkers (e.g., blood markers, DNA sequencing, etc.). This patient information may further inform construction of the patient-specific model.

Once an appropriate patient-specific model is obtained, method 400 may include extracting various features from the model (step 402). As shown in FIG. 4A, step 402 may include extracting geometrical features, image features, hemodynamic features, and/or biomechanical features (of vessel walls and plaque). Image features may be extracted by computing coronary and plaque characteristics and by computing anatomical characteristics. Computed coronary and plaque characteristics may include: APCs, plaque burden (thickness, area, volume, etc.), SYNTAX score, napkin ring, necrotic core, lumen narrowing, minimum lumen diameter (MLD), minimum lumen area (MLA), percentage diameter stenosis, and/or percentage area stenosis. Computed anatomical characteristics may include: epicardial fat volume and/or myocardium shape.

Hemodynamic features may be extracted, for instance, by performing computational flow dynamic analysis for various physiologic conditions (e.g., rest, exercise, hyperemia, etc.) and/or computing hemodynamic characteristics associated with lesions (e.g., max/mean/cyclic wall shear stress, traction, turbulent kinetic energy, etc.). Extracting biomechanical features of vessel wall(s) and plaque may include defining biomechanical properties of vessel wall and plaques based on geometrical and image features (e.g., vessel wall density and elastic properties using linear or nonlinear elasticity model; plaque density and elastic properties using linear or nonlinear elasticity model; and/or ultimate strength of plaque). Using the extracted features, method 400 may include performing computational solid dynamic analysis for various physiologic conditions under steady and/or pulsatile flow (e.g., for rest, exercise, hyperemia, etc.). Method 400 may also include computing tissue stress and strain characteristics in lesions (e.g., max/mean/cyclic stress, ultimate stress, turbulent kinetic energy, etc.) and/or generating a Goodman diagram to identify plaque rupture risk based on mean and alternating stresses. In doing so, step 404 may include creating a feature vector for every point in the patient-specific geometric model, comprising a numerical description of the geometry, biophysical hemodynamic, and wall and plaque biomechanical characteristic at that point, as well as estimates of physiological or phenotypic parameters of the patient. Alternately or in addition, step 404 may include determining every location in the patient-specific geometric model for which plaque vulnerability may be identified, wherein a feature vector is created only for such locations.

Then, step 406 may include producing estimates of cardiac risk, including estimates of the probability of plaque rupture or probability of the event of myocardial infarction at lesions in the patient-specific geometric model. In one embodiment, the estimates are produced using a machine learning technique described in further detail in FIG. 4B. For instance, a prediction system may employ machine-learning techniques to help produce a vulnerability score for one or more locations of coronary lesions. The calculated vulnerability scores may be an application of the machine learning technique in a production mode, separate from a training mode where the machine learning technique processes numerous patient-specific models to develop the ability to make predictions for a target patient.

Finally, method 400 may include step 408 where the estimates are reported to physicians, for instance, in the form of cardiac risk. The cardiac risk discussed including risk of plaque rupture, possibility of an MI event, etc. are merely exemplary instances of cardiac risk. Method 400 may be applied to predicting and reporting any measurement of cardiac risk.

Figure 4B:
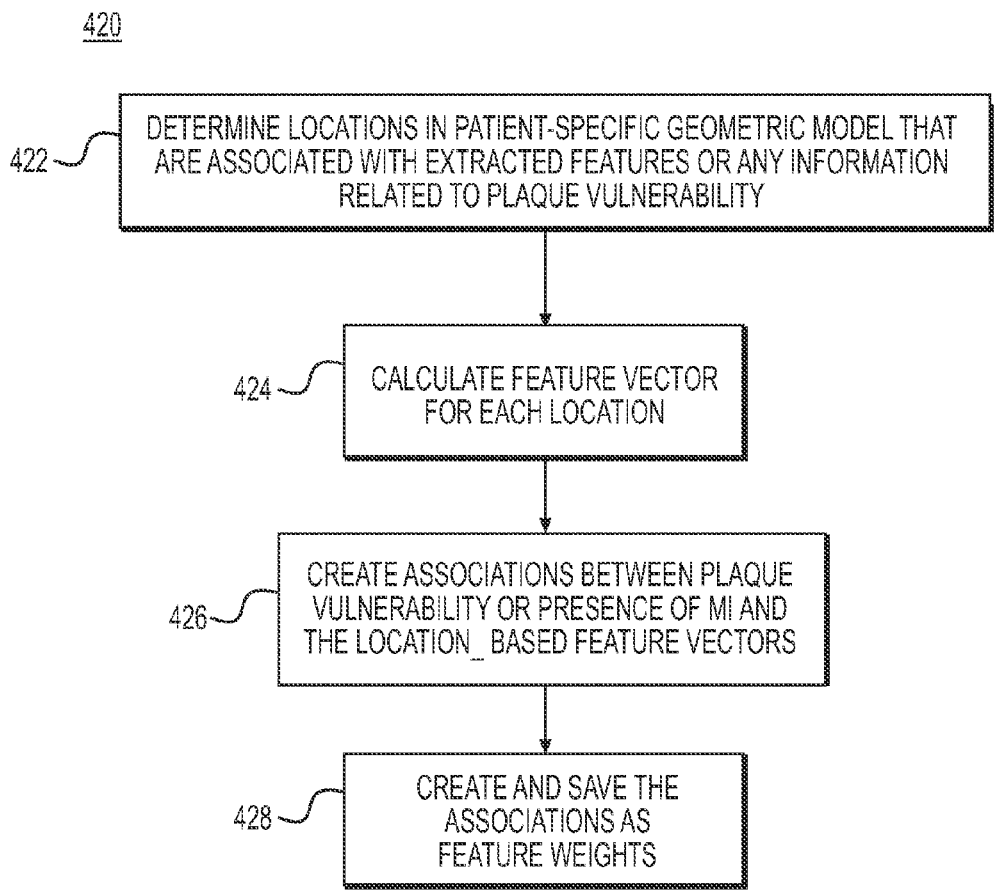
FIG. 4B is a block diagram of an exemplary method for creating and training a prediction system to predict cardiac risk or risk-related features from patient-specific anatomic image data, according to an exemplary embodiment of the present disclosure.

FIG. 4B is a block diagram of an exemplary method 420 for creating and training a prediction system to predict cardiac risk. In one embodiment, the prediction system trained via method 420 may permit the estimates of cardiac risk for method 400. The method of FIG. 4B may be performed by server systems 106, based on information, images, and data received from physicians 102 and/or third party providers 104 over electronic network 100.

As shown in FIG. 4B, method 420 may include obtaining patient-specific models of coronary geometry based on an image of a patient (e.g., CTA). More specifically though, method 420 may involve collecting one or more models in order to create or determine models for comparison to patient-specific models undergoing analysis. In one embodiment, the models may be derived from models associated with individuals, meaning patients other than the patient associated with the patient-specific model undergoing analysis. Aggregating models from a collection of individuals may provide indicators or patterns associated with MI occurrences and/or plaque vulnerability. Method 420 may depict the process of a machine-learning algorithm that continually updates and revises its understanding of indications of plaque vulnerability. In other words, method 420 may be a process of training a prediction system using collected features in order to identify indications of acute myocardial infarction (MI) likelihood over time (if sufficiently large MI patient data were used for training) and/or plaque vulnerability or features of vulnerability measured from OCT, IVUS, and near-infrared spectroscopy (if a surrogate plaque vulnerability model was used for training). The trained prediction system (e.g., a machine learning system) may then be used to test a patient to predict the risk of plaque rupture or myocardial infarction by employing method 400, e.g., by obtaining an image of a patient (e.g., CTA), extracting image/hemodynamic/biomechanical features and calculating risk factors, and sending predicted risk factors to users (e.g., physicians). For example, if the prediction system is trained to predict the vulnerability of one or more locations of one or more locations of coronary lesions, the prediction system may compare models within the prediction system against a patient-specific model associated with a target patient. The comparison may allow the prediction system to estimate vulnerability probabilities for the particular target patient.

In the phase of training a prediction system to assess cardiac risk, training may derive from presence of an MI event associated with a lesion, if there exists a sufficiently large number of MI event patients. If the number of MI events is limited, a surrogate plaque vulnerability model can be used in place of the actual MI events. The surrogate plaque vulnerability model can be utilized from vulnerable features characterized by invasive imaging such as optical coherence tomography (OCT), near infrared spectroscopy (NIRS) and virtual histology intravascular ultrasound (VH-IVUS). An embodiment of method 400 will now be described in detail with reference to an exemplary training mode for the prediction system, such as method 420. In one embodiment, method 420 may begin with determining every location in the various patient-specific geometric models for which there is information about the plaque vulnerability (step 422).

Exemplary Training Mode

For one or more individuals, acquire a digital representation (e.g., the memory or digital storage [e.g., hard drive, network drive] of a computational device such as a computer, laptop, DSP, server, etc.) of the following items for each time point:

Acquire: a patient-specific model of the geometry for the patient's ascending aorta, coronary artery tree, myocardium, valves, and chambers.

Acquire: patient information comprising, at least, estimates of physiological or phenotypic parameters of the patient, including: blood pressure, hematocrit level, patient age, patient gender, myocardial mass, general risk factors of coronary artery disease, and/or one or more biomarkers. The myocardial mass may be derived by segmenting the myocardium in the image, calculating the volume in the image, and using an estimated density of 1.05 g/mL to estimate the myocardial mass.

The general risk factors of coronary artery disease may include: smoking, diabetes, hypertension, lipid level (e.g., low density lipoprotein (LDL) cholesterol (LDL-C) levels), dietary habits, family history, physical activity, sexual activity, weight (abdominal obesity), cholesterol, and/or stress state (e.g., depression, anxiety, or distress).

The biomarkers may include: complement reactive protein (CRP), fibrinogen, WBC (White blood cell) count, matrix metalloproteinase (e.g., MMP-9, MMP-3 polymorphism), IL-6, IL-18, and TCT-α (Cytokines), circulating soluble CD40 Ligand (sCD40L), and/or Vascular Calcification Markers (e.g., Osteopontin).

Acquire: image features from CT, including: plaque burden (thickness, area, volume), SYNTAX score, napkin ring, and/or necrotic core Acquire: one or more estimates of biophysical hemodynamic characteristic from computational fluid dynamics analysis. Computational fluid dynamics to simulate blood flow have been well studied. The estimates in this embodiment include:

Simulation condition (e.g., rest, exercise (Low/Medium/High grade by changing degree of cardiac output), hyperemia, etc.).

Hemodynamic Quantity:

Max, cyclic wall-shear stress and mean wall-shear stress, defined as $$\left| \frac{1}{T_1 - T_0} \int_{T_0}^{T_1} \vec{t_s} \, dt \right|,$$

where $\vec{t_s}$ is the wall shear stress vector defined as the in-plane component of the surface traction vector.

Turbulent kinetic energy (TKE). This quantity is a measure of the intensity of turbulence associated with eddies in turbulent flow, and is characterized by measured root-mean-square velocity fluctuation. TKE can be normalized by kinetic energy.

Acquire: one or more estimates of vessel wall and plaque biomechanical characteristic from computational solid dynamics analysis. The estimates in this embodiment may include: simulation condition (pulsatile or steady flow) (rest, exercise (Low/Medium/High grade by changing degree of cardiac output), and/or hyperemia; biomechanical material properties of vessel wall and plaque derived from literature data and/or image characteristics (e.g., linear elastic, nonlinear elastic, viscoelastic constitutive models, density, compressible or incompressible material behavior, and/or ultimate strength of material; and biomechanical stress and strain (e.g., max or mean cyclic wall and plaque stress, max or mean cyclic wall and plaque strain, and/or alternating stress and strain).

Acquire: location(s) of plaque at culprit lesion being targeted for prediction of vulnerability. The location of plaque can be determined by use of CT and other imaging modalities including intravascular ultrasound, or optical coherence tomography.

Step 422 may thus include determining every location in the various patient-specific geometric models for which there is information about the plaque vulnerability. Then, step 424 may include creating a feature vector for each location that contains a numerical description of physiological or phenotypic parameters of the patient and a description of the local geometry and biophysical hemodynamic characteristic. Specifically the feature vector may contain:

Systolic and diastolic blood pressure

Heart rate

Blood properties including: plasma, red blood cells (erythrocytes), hematocrit, white blood cells (leukocytes) and platelets (thrombocytes), viscosity, yield stress Patient age, gender, height, weight Lifestyle characteristics: presence or absence of current medications/drugs General risk factors of CAD, such as: smoking status, diabetes, hypertension, lipid level (e.g., low density lipoprotein (LDL) cholesterol (LDL-C) levels), dietary habits, family history, physical activity, sexual activity, weight (abdominal obesity), cholesterol, and/or stress state (e.g., depression, anxiety or distress)

Biomarkers, such as: complement reactive protein (CRP), fibrinogen, WBC (White blood cell), matrix metalloproteinase (e.g., MMP-9, MMP-3 polymorphism), IL-6, IL-18, and TCT-α (Cytokines), circulating soluble CD40 Ligand (sCD40L), vascular calcification markers (e.g., Osteopontin).

Amount of calcium in aorta and valve

Presence of aortic aneurysm

Presence of valvular heart disease

Presence of peripheral disease

Epicardial fat volume

Cardiac function (ejection fraction)

Characteristics of the aortic geometry, e.g., cross-sectional area profile along the ascending and descending aorta, and/or surface area and volume of the aorta SYNTAX score Characteristics of coronary lesion, e.g., minimum lumen area, minimum lumen diameter, degree of stenosis at lesion (percentage diameter/area stenosis), e.g., by determining virtual reference area profile by using Fourier smoothing or kernel regression, and/or computing percentage stenosis of lesion using the virtual reference area profile along the vessel centerline; location of stenotic lesions, such as by computing the distance (parametric arc length of centerline) from the main ostium to the start or center of the lesion; length of stenotic lesions, such as by computing the proximal and distal locations from the stenotic lesion, where cross-sectional area is recovered; and/or irregularity (or circularity) of cross-sectional lumen boundary.

Characteristics of coronary lumen intensity at lesion, e.g., based on intensity change along the centerline (slope of linearly-fitted intensity variation)

Characteristics of surface of coronary geometry at lesion, e.g., based on 3-D surface curvature of geometry (Gaussian, maximum, minimum, mean), e.g., based on characteristics of coronary centerline (topology) at lesion:

Curvature (bending) of coronary centerline
Compute Frenet curvature $$\kappa = \frac{|p' \times p''|}{|p'|^3},$$

where p is coordinate of centerline parameterized by cumulative arc-length to the starting point
Compute an inverse of the radius of a circumscribed circle along the centerline points Tortuosity (non-planarity) of coronary centerline
Compute Frenet torsion $$\tau = \frac{(p' \times p'') \cdot p'''}{|p' \times p''|^2},$$

where p is coordinate of centerline

Characteristics of coronary deformation (possibly involving multi-phase CCTA (e.g., diastole and systole)): distensibility of coronary artery over cardiac cycle; bifurcation angle change over cardiac cycle; and/or curvature change over cardiac cycle Characteristics of existing plaque: location of plaque along centerline (distance to closest upstream bifurcation point, and/or bifurcation angle of coronary branches if plaque is located at the bifurcation), adverse plaque characteristics (presence of positive remodeling, presence of low attenuation plaque, and/or presence of spotty calcification), plaque burden (thickness, area, and/or volume), presence of Napkin ring, intensity of plaque, type of plaque (calcified, non-calcified), distance from the plaque location to ostium (LM or RCA), and/or distance from the plaque location to the nearest downstream/upstream bifurcation.

Characteristics of coronary hemodynamics derived from computational flow dynamics or invasive measurement: To obtain transient characteristics of blood, pulsatile flow simulation may be performed by using a lumped parameter coronary vascular model for downstream vasculatures, inflow boundary condition with coupling a lumped parameter heart model and a closed loop model to describe the intramyocardial pressure variation resulting from the interactions between the heart and arterial system during cardiac cycle.

Measured FFR
Pressure gradient
FFRct
Maximum, cyclic and mean wall-shear stress
Turbulent kinetic energy
Local flow rate Characteristics of wall and plaque biomechanics derived from computational solid dynamics: plaque mean, max and alternating stress and strain, and/or ultimate stress and strength Once feature vector creation is completed in step 424, step 426 may include associating the feature vector with available models of plaque vulnerability at the same location. Such models may include surrogate vulnerable feature models. The following surrogate vulnerable features can be available at the time when cardiac images were acquired by invasive imaging such as OCT, NIRS, or VH-IVUS:

Thin cap fibroatheroma (TCFA)<65 microns
Large necrotic core
a. 25% of plaque area
b. >120 degree circumference
c. 2-22 mm long
Speckled pattern of calcification
Macrophages As part of step 426, the associations created between feature vectors and models may permit recognition of trends, similarities, and/or groupings of various factors that may indicate plaque vulnerability or likelihood or presence of MI events at specific points. In one embodiment, step 426 may include quantifying the associations as feature weights, such that relationships between various factors that play into cardiac risk can be returned as predictions. In other words, the prediction system may assign or combine feature vectors with weights. Part of the training aspect of the prediction system may include continually adjusting feature weights for better accuracy in predictions. Thus, step 426 may include training a machine-learning algorithm (e.g. a linear SVM) to learn the associations and/or feature weights in order to predict plaque vulnerability or presence of MI event at points on a model.

Then for step 428, results (e.g. feature weights) of the machine learning algorithm-based prediction system may be continually saved as a digital representation (e.g., the memory or digital storage (e.g., hard drive, network drive) of a computational device such as a computer, laptop, DSP, server, etc.). Step 428 may include continually updating feature weights as more patient-specific models are collected and feature vectors constructed. Step 428, therefore, permits a prediction system that continually incorporates features input from acquired patient-specific models.

Exemplary Application of Prediction System

For a target patient, an exemplary method may include acquiring a digital representation (e.g., the memory or digital storage (e.g., hard drive, network drive) of a patient-specific model of the geometry for the patient's ascending aorta, coronary artery tree, myocardium, valves, and chambers. This geometry may be represented as a list of points in space (possibly with a list of neighbors for each point) in which the space can be mapped to spatial units between points (e.g., millimeters). This model may be derived by performing a cardiac CT imaging of the patient in the end diastole phase of the cardiac cycle. This image then may be segmented manually or automatically to identify voxels belonging to the aorta and the lumen of the coronary arteries. Once the voxels are identified, the geometric model can be derived (e.g., using marching cubes). The process for generating the patient-specific model of the geometry may be the same as in the training mode. A list of physiological and phenotypic parameters of the patient may be obtained during training mode.

For every point in the patient-specific geometric model, the exemplary method may include creating a feature vector for that point including a numerical description of the geometry and biophysical hemodynamic and wall and plaque biomechanical characteristic at that point, and estimates of physiological or phenotypic parameters of the patient. These features may be the same as the quantities used in the training mode.

The exemplary method may include using the saved results of the machine-learning algorithm produced in the training mode (e.g., feature weights) to produce estimates of the probability of the plaque rupture or MI event at lesions in the patient-specific geometric model. These estimates may be produced using the same machine learning technique used in the training mode. The exemplary method may include saving the predicted probability of the plaque vulnerability (rupture) for lesions or MI event to a digital representation (e.g., the memory or digital storage (e.g., hard drive, network drive) of a computational device such as a computer, laptop, DSP, server, etc.), and communicating the patient-specific risk factors to a health care provider.

FIG. 5A is a block diagram of an exemplary method 500 for medical therapy planning and lifestyle management. The method of FIG. 5A may be performed by server systems 106, based on information, images, and data received from physicians 102 and/or third party providers 104 over electronic network 100. In one embodiment, FIG. 5A may be an extension of the understanding of cardiac risk developed from methods 400 and 420. For instance, method 500 may determine the impact of various medical therapies or treatments and/or lifestyle modifications on lowering cardiac risk. More specifically, method 500 may involve determining the effect of medical therapies or lifestyle modifications on the features used in the cardiac risk predictions. As shown in FIG. 5A, method 500 may first include, retrieving features used in method 400 to predict cardiac risk prediction (step 502). For step 504, various medical therapy, protocols, and/or lifestyle modifications may be determined. For instance, medical therapies may include anti-ischemic drugs for ischemia management, antiplatelet agents, and/or lipid-lowering agents for event prevention, etc. Anti-ischemic drugs may include nitrates, beta-blockers (e.g., metoprolol, bisoprolol, antenolol, etc.), ivabradine, etc. Exemplary antiplatelet agents may include low-dose aspirin, while lipid-lowering agents may include statin treatments. Lifestyle modifications may include: smoking cessation, diet control, physical and/or sexual activity, weight management, arterial hypertension management, and stress management.

Step 506 may include determining the effect of a given medical therapy, protocol, or lifestyle modification on the features used in computed plaque vulnerability prediction. For example, effects for lifestyle modifications and control of risk factors may be as follows:

Smoking cessation: can reduce systolic pressure by 3.5+/−1.1 mmHg and diastolic pressure by 1.9+/−0.7 mmHg and reduce heart rate by 7.3+/−1.0 beats/min [18].

Diet control: N-3 polyunsaturated fatty acid (PUFA) consumption (e.g., from oily fish) can reduce triglycerides; and decreased triglycerides level can reduce blood viscosity by 2%.

Physical activity: regular physical activity can reduce blood pressure by 3 mmHg; regular physical activity can cause plaque regression.

Sexual activity: sexual activity is associated with 75% of exercise workload in systolic BP; regular sexual activity can reduce blood pressure by 2 mmHg.

Weight management: weight reduction in obese people can decrease BP by 10% and reduce blood viscosity by 2%.

Arterial hypertension management: reductions in blood pressure of 10-12 mmHg systolic and 5-6 mmHg diastolic can decrease coronary artery disease of 16%.

Stress management: relief of depression, anxiety, and distress can reduce symptoms resulting in 10% HR and blood pressure reduction.

Effects for anti-ischemic drugs for ischemia management may include:

Nitrates: 5% increase in diameter of epicardial coronary arteries for sublingual nitroglycerin (GTN) capsules and 13% increase in diameter of epicardial coronary arteries for isosorbide dinitrate (ISDN).

Beta-blockers (e.g., metoprolol, bisoprolol, atenolol): reduction of heart rate by 10%; Reduction of blood pressure by 10%.

Ivabradine: reduction of heart rate by 8.1+/−11.6 beats/min

Effects associated with antiplatelet agents for event prevention may be: low-dose aspirin; reduce blood pressure by 20 mmHg Impact of lipid-lowering agents for event prevention may include: statin treatment reduces low density lipoprotein (LDL) cholesterol (LDL-C) levels and thus decrease blood viscosity by 2%.

Step 506 may include determining the effects on features (e.g. from or relating to feature vectors) for a target patient (based a respective patient-specific model). Method 500 may thus determine the effect of a given medical therapy protocol or lifestyle modification on the features used in computed plaque vulnerability prediction (step 506). Method 500 may further include providing an optimal treatment protocol to a physician based on the effect of one or more treatment protocols on the risk factor prediction (step 508). In one embodiment, step 508 may optionally include producing a rendering of the effects of various treatment protocols such that a physician may compare protocols and projections of effects on the features based on the protocols. A further embodiment of step 508 may include analyzing the combined effects of multiple treatment protocols and/or lifestyle modifications such that physicians may offer a treatment regimen that may include more than one form of therapy.

FIG. 5B is a block diagram of an exemplary method 520 by which a machine learning algorithm may determine effects of various medical treatments and/or lifestyle modifications on the features. The method of FIG. 5B may be performed by server systems 106, based on information, images, and data received from physicians 102 and/or third party providers 104 over electronic network 100. Essentially, method 520 describes one embodiment of step 506 of method 500 in more detail. In one embodiment, method 500 for guiding medical therapy may use a machine-learning based cardiac risk predictor established in the method of FIG. 4B and add an additional layer of machine-based learning by evaluating patient-specific cardiac imaging models through medical therapy and lifestyle modifications. Therefore, method 520 may help predict, for instance, the probability of plaque rupture risk using updated features and a trained machine-learning algorithm.

For example, method 520 may include employing patient-specific models reflecting the geometry of the patient-specific model used in method 420 of training the cardiac risk prediction system, including the list of physiological and phenotypic parameters of the patient (e.g., obtained during training mode for the cardiac event predictor). In other words, patient-specific models used in method 520 may include geometry of ascending aortas, coronary artery trees, myocardium, valves, and chambers respective to each patient.

For every point in each patient-specific geometric model, method 520 may include feature vectors for each point, comprising a numerical description of the geometry and biophysical hemodynamic and biomechanical characteristic at that point, and estimates of physiological or phenotypic parameters of the patient. These features may be the same as the quantities used in the training mode for the cardiac risk prediction system.

Step 522 may include virtually adjusting feature sets to simulate application of medical therapies or lifestyle modifications to patient-specific models. Then for step 524, method 520 may estimate probability of cardiac risk according to the adjustments. In one embodiment, step 524 may rely on the saved results of the machine-learning algorithm produced in the training mode (e.g., feature weights) to produce estimates of the probability. These estimates may be produced using the same machine-learning algorithm used in the training mode for the cardiac event predictor. For example, if beta-blocker (e.g., metoprolol, bisoprolol, atenolol) is chosen for a medical therapy, the algorithm may update the following features: reduce blood pressure by 10% and heart rate by 10% and/or update boundary conditions for coronary blood flow simulation and extract new hemodynamics and wall and plaque biomechanical features.

Based on the estimates, step 526 may include a comparison of estimates for various applied protocols and modifications. In one embodiment, step 526 may include a second machine-learning algorithm specifically applied to the effects of treatment given various combinations of features and/or feature vectors. For example, this second machine-learning algorithm may be an extension of the first machine-learning algorithm for cardiac risk. In another instance, the second machine-learning algorithm may be a separate, independent entity. In such a case, the models on which the machine learning algorithms are constructed may be independent and/or overlap.

Step 528 may include determining an optimal treatment and/or lifestyle modification based on the comparison from step 526. Optimal treatments may be based simply on the effects of optimal treatments and/or lifestyle modifications on features. In a further embodiment, the optimal treatments may take into account patient-specific factors. For instance, step 528 may include determining a patient's geographical location and determining optimal treatment in light of the location. For example, a patient that lives near a beach may have an optimal lifestyle modification involving swimming whereas such a recommendation may be less optimal for a land-locked patient. The optimal treatments may further consider other patient treatments. For example, running or walking may be a lifestyle modification that best suits a patient based on the effects of the modification on a patient's factors. However, it may not be practical for a patient with a recent knee injury to employ such a modification. Step 528 may thus create an optimal treatment, with respect to a patient's specific conditions. Step 528 may further include saving the predicted probability of the plaque vulnerability (rupture) for lesions to a digital representation (e.g., the memory or digital storage (e.g., hard drive, network drive) of a computational device such as a computer, laptop, DSP, server, etc.) for a given medical therapy. In relation to step 508 of method 500, step 508 may include outputting to a doctor the effect of one or more treatment protocols on the risk factor prediction and suggesting optimal treatment protocol based on the predicted plaque vulnerability determined in step 528.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of determining an effect of a treatment on coronary plaque vulnerability, the method comprising:
    acquiring anatomical image data of at least part of a patient's vascular system;
    performing, using a processor, an analysis including image characteristics analysis, geometrical analysis, computational fluid dynamics analysis, and structural mechanics analysis on the anatomical image data;
    predicting, using the processor, a coronary plaque vulnerability defining a risk of rupture of one or more regions of plaque present in the patient's vascular system based on results of the analysis including the image characteristics analysis, geometrical analysis, computational fluid dynamics analysis, and structural mechanics analysis of the anatomical image data;
    modifying the analysis including the image characteristics analysis, geometrical analysis, computational fluid dynamics analysis, and structural mechanics analysis on the anatomical image data based on a proposed treatment; and
    determining an effect of the treatment on the predicted coronary plaque vulnerability defining the risk of rupture of the one or more regions of plaque, based on the modified analysis including the image characteristics analysis, geometrical analysis, computational fluid dynamics analysis, and structural mechanics analysis on the anatomical image.

2. The method of claim 1, further including:
    acquiring, for each of a plurality of individuals, individual-specific anatomic data and blood flow characteristics of at least part of the individual's vascular system; and
    predicting risk of plaque rupture or myocardial infarction based on the individual-specific anatomic data and blood flow characteristics for each of the plurality of individuals,
    wherein the determining of the effect of the treatment is based on the risk of plaque rupture or myocardial infarction.

3. The method of claim 1, further including:
    generating a patient-specific geometric model of at least part of the patient's vascular system;
    extracting, using a processor, geometrical features, image features, hemodynamic characteristics of blood flow through the patient-specific geometric model, and/or biomechanical features associated with the geometric model; and
    predicting, using the processor, cardiac risk, based on results of the extraction of geometrical features, image features, hemodynamic characteristics of blood flow through the patient-specific geometric model, and/or biomechanical features associated with the geometric model.

4. The method of claim 3, further including:
    acquiring one or more physiological and/or phenotypic parameters;
    obtaining one or more geometric qualities of one or more coronary arteries of the patient-specific geometric model of the patient's vascular system; and
    determining presence or absence of plaque vulnerability at each of a plurality of locations in the patient-specific geometric model of the patient's vascular system.

5. The method of claim 4, further including:
    generating one or more patient feature vectors based on the geometrical features, image features, the hemodynamic characteristics, the biomechanical features, and/or the one or more physiological and/or phenotypic parameters,
    wherein the one or more patient feature vectors are associated with each of the plurality of locations and/or each of the plurality of locations associated with the determined presence of plaque vulnerability.

6. The method of claim 5, further including:
    determining one or more treatments; and determining an association between the one or more patient feature vectors, the one or more treatments, one or more known indicators of cardiac risk, or a combination thereof, wherein the determining of the effect of the treatment is based on the association between the one or more patient feature vectors, the one or more treatments, one or more known indicators of cardiac risk, or a combination thereof.

7. The method of claim 6, further including:

adjusting one or more feature sets associated with the one or more patient feature vectors, wherein the determining of the effect of the treatment on the predicted coronary plaque vulnerability is further based on the step of adjusting one or more feature sets associated with the one or more patient feature vectors.

8. The method of claim 6, further including:

generating a presentation of at least a portion of the one or more treatments or the effect of the treatment for each treatment of the portion of the one or more treatments.

9. A system of determining an effect of a treatment on coronary plaque vulnerability, the system comprising:

a data storage device storing instructions for predicting coronary plaque vulnerability from patient-specific anatomic image data; and a processor configured to execute the instructions to perform a method including:

acquiring anatomical image data of at least part of the patient's vascular system;

performing, using a processor, an analysis including image characteristics analysis, geometrical analysis, computational fluid dynamics analysis, and structural mechanics analysis on the anatomical image data;

predicting, using the processor, a coronary plaque vulnerability defining a risk of rupture of one or more regions of plaque present in the patient's vascular system based on results of the analysis including the image characteristics analysis, geometrical analysis, computational fluid dynamics analysis, and structural mechanics analysis of the anatomical image data;

modifying the analysis including the image characteristics analysis, geometrical analysis, computational fluid dynamics analysis, and structural mechanics analysis on the anatomical image data based on a proposed treatment; and determining an effect of the treatment on the predicted coronary plaque vulnerability defining the risk of rupture of one or more regions of plaque, based on the modified analysis including image characteristics analysis, geometrical analysis, computational fluid dynamics analysis, and structural mechanics analysis on the anatomical image.

10. The system of claim 9, wherein the processor is further configured for:

acquiring, for each of a plurality of individuals, individual-specific anatomic data and blood flow characteristics of at least part of the individual's vascular system; and predicting risk of plaque rupture or myocardial infarction based on the individual-specific anatomic data and blood flow characteristics for each of the plurality of individuals, wherein the determining of the effect of the treatment is based on the risk of plaque rupture or myocardial infarction.

11. The system of claim 9, wherein the processor is further configured for:

generating a patient-specific geometric model of at least part of the patient's vascular system;

extracting, using a processor, geometrical features, image features, hemodynamic characteristics of blood flow through the patient-specific geometric model, and/or biomechanical features associated with the geometric model; and predicting, using the processor, cardiac risk, based on results of the extraction of geometrical features, image features, hemodynamic characteristics of blood flow through the patient-specific geometric model, and/or biomechanical features associated with the geometric model.

12. The system of claim 11, wherein the processor is further configured for:

acquiring one or more physiological and/or phenotypic parameters;

obtaining one or more geometric qualities of one or more coronary arteries of the patient-specific geometric model of the patient's vascular system; and determining a presence or absence of plaque vulnerability at each of a plurality of locations in the patient-specific geometric model of the patient's vascular system.

13. The system of claim 12, wherein the processor is further configured for:

generating one or more patient feature vectors based on the geometrical features, image features, the hemodynamic characteristics, the biomechanical features, and/or the one or more physiological and/or phenotypic parameters, wherein the one or more patient feature vectors are associated with each of the plurality of locations and/or each of the plurality of locations associated with the determined presence of plaque vulnerability.

14. The system of claim 13, wherein the processor is further configured for:

determining one or more treatments; and determining an association between the one or more patient feature vectors, the one or more treatments, one or more known indicators of cardiac risk, or a combination thereof, wherein the determining of the effect of the treatment is based on the association between the one or more patient feature vectors, the one or more treatments, one or more known indicators of cardiac risk, or a combination thereof.

15. The system of claim 14, wherein the processor is further configured for:

adjusting one or more feature sets associated with the one or more patient feature vectors, wherein the determining of the effect of the treatment on the predicted coronary plaque vulnerability is further based on the step of adjusting one or more feature sets associated with the one or more patient feature vectors.

16. The system of claim 14, wherein the processor is further configured for:

generating a presentation of at least a portion of the one or more treatments or the effect of the treatment for each treatment of the portion of the one or more treatments.

17. A non-transitory computer readable medium for use on a computer system containing computer-executable programming instructions for performing a method of determining the effect of a treatment on coronary plaque vulnerability, the method comprising:

acquiring anatomical image data of at least part of the patient's vascular system;

performing, using a processor, an analysis including image characteristics analysis, geometrical analysis, computational fluid dynamics analysis, and structural mechanics analysis on the anatomical image data;

predicting, using the processor, a coronary plaque vulnerability defining a risk of rupture of one or more regions of plaque present in the patient's vascular system based on results of the analysis including the image characteristics analysis, geometrical analysis, computational fluid dynamics analysis, and structural mechanics analysis of the anatomical image data;

modifying the analysis including the image characteristics analysis, geometrical analysis, computational fluid dynamics analysis, and structural mechanics analysis on the anatomical image data based on a proposed treatment; and determining an effect of the treatment on the predicted coronary plaque vulnerability defining the risk of rupture of one or more regions of plaque, based on the modified analysis including the image characteristics analysis, geometrical analysis, computational fluid dynamics analysis, and structural mechanics analysis on the anatomical image.

18. The non-transitory computer readable medium of claim 17, the method further comprising:

acquiring, for each of a plurality of individuals, individual-specific anatomic data and blood flow characteristics of at least part of the individual's vascular system; and predicting risk of plaque rupture or myocardial infarction based on the individual-specific anatomic data and blood flow characteristics for each of the plurality of individuals, wherein the determining of the effect of the treatment is based on the risk of plaque rupture or myocardial infarction.

19. The non-transitory computer readable medium of claim 17, the method further comprising:

generating a patient-specific geometric model of at least part of the patient's vascular system;

extracting, using a processor, geometrical features, image features, hemodynamic characteristics of blood flow through the patient-specific geometric model, and/or biomechanical features associated with the geometric model; and predicting, using the processor, cardiac risk, based on results of the extraction of geometrical features, image features, hemodynamic characteristics of blood flow through the patient-specific geometric model, and/or biomechanical features associated with the geometric model.

20. The non-transitory computer readable medium of claim 19, the method further comprising:

acquiring one or more physiological and/or phenotypic parameters;

obtaining one or more geometric qualities of one or more coronary arteries of the patient-specific geometric model of the patient's vascular system; and determining a presence or absence of plaque vulnerability at each of a plurality of locations in the patient-specific geometric model of the patient's vascular system.

\* \* \* \* \*